US012691031B2

(12) United States Patent
Li et al.

(10) Patent No.: US 12,691,031 B2
(45) Date of Patent: Jul. 28, 2026

(54) POSITIVE-PRESSURE DOUBLE-NOZZLE NASAL CAVITY CLEANER FEATURING DOUBLE PRESSURE PROTECTION AND USE METHOD THEREOF

(71) Applicant: Shanghai Sonmol Internet Technology Co., Ltd., Shanghai City (CN)

(72) Inventors: YongXu Li, Mianyang City (CN); Liang Lv, Chongqing City (CN); JiGuang Zhang, Xiangyang City (CN)

(73) Assignee: Shanghai Sonmol Internet Technology Co., Ltd., Shanghai (CN)

( * ) Notice: Subject to any disclaimer, the term of this patent is extended or adjusted under 35 U.S.C. 154(b) by 730 days.

(21) Appl. No.: 17/977,141

(22) Filed: Oct. 31, 2022

(65) Prior Publication Data

US 2024/0122801 A1 Apr. 18, 2024

(30) Foreign Application Priority Data

Oct. 14, 2022 (CN) .......................... 202211262165.7

(51) Int. Cl.
*A61H 35/04* (2006.01)

(52) U.S. Cl.
CPC ....... *A61H 35/04* (2013.01); *A61H 2205/023* (2013.01); *A61M 2210/0618* (2013.01)

(58) Field of Classification Search
CPC ............. A61H 35/04; A61H 2205/023; A61M 2210/0618

(Continued)

(56) References Cited

U.S. PATENT DOCUMENTS 4,605,400 A * 8/1986 Kurtz ...................... A61M 1/61
604/319
6,907,879 B2 * 6/2005 Drinan ................... A61B 5/411
604/35

(Continued)

FOREIGN PATENT DOCUMENTS

WO WO-2021222866 A1 * 11/2021 ............ B01L 3/5029

*Primary Examiner* — Philip E Stimpert

(57) ABSTRACT

The present invention discloses a positive-pressure double-nozzle nasal cavity cleaner featuring double pressure protection, and relates to the technical field of health care. The nasal cavity cleaner consists of a nose washing end, an upper shell, a core module, a control module, a lower shell, a liquid reservoir and a waste reservoir, wherein the nose washing end is rotatably connected to a top portion of the upper shell, and the nose washing end consists of a silicone washing nozzle, a silicone backflow nozzle and a rotary connecting base. The nasal cavity cleaner uses positive pressure and automatic pressure relief structures to obtain safe and constant air pressure, and then presses normal saline into the nasal cavity to clean the nasal cavity, so that pressure in the nasal cavity is small and stable during cleaning, which prevents damage to the nasal cavity and ear canal, thus being safer to use. Besides, deeper areas can be washed, nasal scabs in the nasal cavity can be moistened and removed, harmful substances such as dust in the nasal cavity can be removed, the nasal cavity can be moistened, and normal swing of nasal cilia can be recovered, which are helpful in treating rhinitis and preventing the onset of allergic rhinitis.

17 Claims, 15 Drawing Sheets

(58) Field of Classification Search
USPC ....... 604/27, 30, 39, 41, 94.01; 137/12, 156;
417/41, 65, 120, 385, 388
See application file for complete search history.

(56) References Cited

U.S. PATENT DOCUMENTS

| | | | | |
|---|---|---|---|---|
| 2008/0221507 | A1* | 9/2008 | Hoke ...................... | A61P 11/02 |
| | | | | 604/35 |
| 2012/0330239 | A1* | 12/2012 | Hoke ...................... | A61M 1/77 |
| | | | | 604/151 |
| 2015/0053272 | A1* | 2/2015 | Weinzierl ................. | F17D 1/12 |
| | | | | 137/156 |

* cited by examiner

Sealing ring for valve
element air channel

Adjustment screw

Umbrella-shaped rubber pad
fixer

Valve element air channel

Umbrella-shaped rubber pad

DC-
DC
mod
ule

POSITIVE-PRESSURE DOUBLE-NOZZLE NASAL CAVITY CLEANER FEATURING DOUBLE PRESSURE PROTECTION AND USE METHOD THEREOF

TECHNICAL FIELD

The present invention relates to the technical field of health care, in particular to a positive-pressure double-nozzle nasal cavity cleaner featuring double pressure protection and a use method thereof.

BACKGROUND

Double-nozzle nasal irrigators available on the market currently are based on negative pressure. The nasal irrigator is used by directly starting an air pump, so that a cleaning liquid is induced under negative pressure to enter one nostril, then bypass the rear edge of the nasal septum, and finally flow out from the other nostril and be sucked into a waste liquid receiver. The device produces a strong impact water flow at the start-up moment and in the use process, which may cause great irritation to the nasal cavity and eardrum, making users feel uncomfortable and even fearful.

SUMMARY

The purpose of the present invention is to provide a double-nozzle positive-pressure nasal cavity cleaner featuring automatic pressure relief protection, so as to solve the problems of incomplete cleaning and potential safety hazards in the nose wash cleaning and water column irrigation methods described in the above background art.

In order to achieve the above purpose, the present invention is realized by the following technical scheme of a positive-pressure double-head nasal cavity cleaner featuring double pressure protection, including a cleaning liquid container, a nose connecting part and a waste liquid recovery container, wherein the positive-pressure double-nozzle nasal cavity cleaner further includes a positive pressure source, which drives a cleaning liquid to flow by increasing air pressure in the cleaning liquid container, an automatic pressure relief mechanism is arranged in an internal passage of the positive pressure source to maintain the air pressure, the automatic pressure relief mechanism includes a mechanical pressure relief part and an electronic feedback part, the electronic feedback part and a driving part in the positive pressure source are controlled by a control module, and the control module stabilizes hydraulic pressure in a liquid passage at a preset value.

Optionally, the positive pressure source, the automatic pressure relief mechanism and the control module are located in a shell of the cleaner, and the nose connecting part, the cleaning liquid container and the waste liquid recovery container are all detachably connected to the shell of the cleaner.

Optionally, the nose connecting part includes two silicone nozzles, and when the two silicone nozzles are inserted into the nasal cavity, a flow passage of liquid flowing out of the cleaning liquid container, passing through the nasal cavity and then flowing into the waste liquid recovery container is formed.

Optionally, the mechanical pressure relief part is a pressure relief valve, and a preset pressure value of the pressure relief valve is adjustable.

Optionally, the electronic feedback part includes an air pressure sensor arranged in a passage of the positive pressure source, the air pressure sensor sends air pressure data to a feedback module, and the control module adjusts an output of the positive pressure source according to the air pressure data received by the feedback module to stabilize water pressure in the water passage.

Optionally, the feedback module is provided with at least two settings, which are controlled by switches, and each setting corresponds to a preset water pressure value.

The present invention further provides a use method of a positive-pressure double-nozzle nasal cavity cleaner featuring double pressure protection, including the following steps:

S1. checking whether the cleaner is able to work properly;

S2. after confirming that the cleaner is able to work properly, preparing a nasal wash and loading the nasal wash into the cleaner, wherein an appropriate amount of warm normal saline is loaded into a liquid reservoir as needed;

S3. installing the liquid reservoir onto a cleaner body;

S4. holding the cleaner with a key facing a human body, and moving a nose washing end slowly toward nostrils so as to be inserted into the nostrils, and ensuring that the nose washing end completely blocks the nostrils;

S5. pressing the key to start nasal cavity cleaning; and

S6. removing a waste reservoir.

Optionally, the temperature of the cleaning liquid in S2 is 37° C.

Optionally, in S1, it is checked whether there is a battery in a battery compartment, and it is checked whether mode one and mode two keys of an integrated soft rubber key on an upper shell function properly based on indicator lights activated by pressing the key.

The present invention provides a positive-pressure double-nozzle nasal cavity cleaner featuring double pressure protection. Beneficial effects are as follows:

(1) The positive-pressure double-nozzle nasal cavity cleaner featuring double pressure protection uses positive pressure and automatic pressure relief structures to obtain safe and constant air pressure, and then presses normal saline into the nasal cavity to clean the nasal cavity, so that pressure in the nasal cavity is small and stable during cleaning, which prevents damage to the nasal cavity and ear canal, thus being safer to use.

(2) The positive-pressure double-nozzle nasal cavity cleaner featuring double pressure protection can clean the nasal cavity without harming the nasal cavity. Besides, deeper areas can be washed, nasal scabs in the nasal cavity can be moistened and removed, harmful substances such as dust in the nasal cavity can be removed, the nasal cavity can be moistened, and normal swing of nasal cilia can be recovered, which are helpful in treating rhinitis and preventing the onset of allergic rhinitis.

Figure 1:
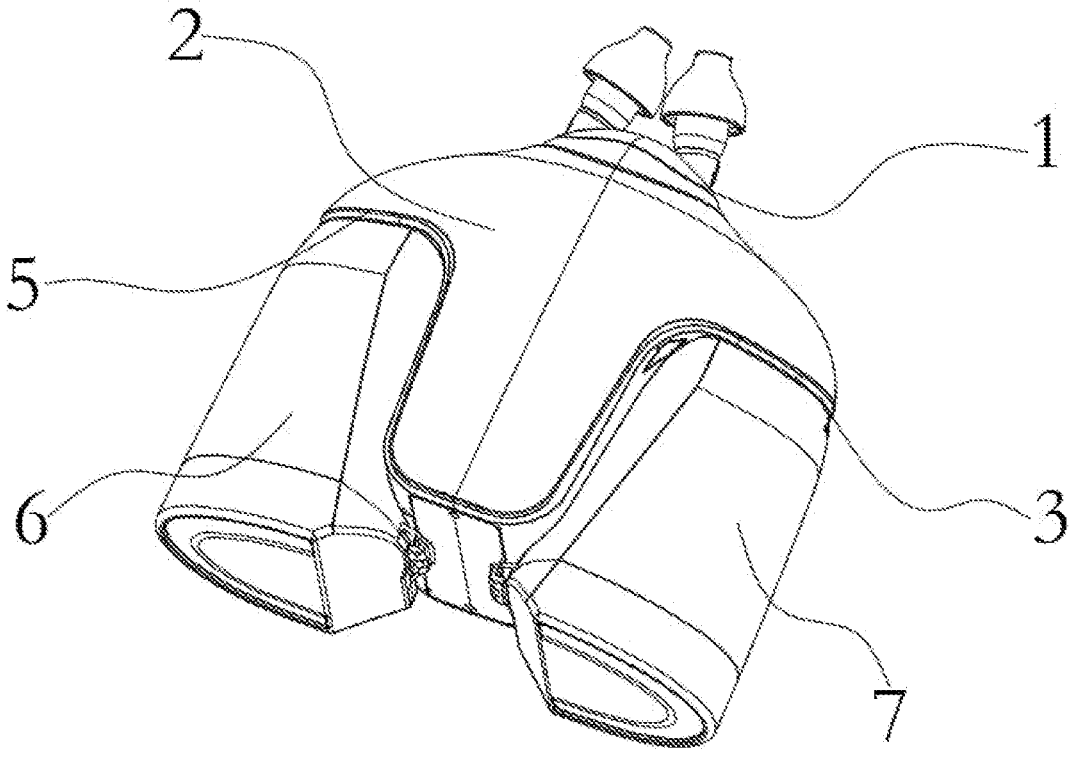
FIG. 1 is a schematic diagram of the overall appearance of a nasal cavity cleaner of the present invention.

In the accompanying drawings: 1 Nose washing end, 101 Silicone washing nozzle, 102 Silicone backflow nozzle, 103 Rotary connecting base, 104 Water pipe connector, 2 Upper shell, 201 Integrated soft rubber key, 202 Waste reservoir vent hole, 3 Core module, 301 Air pump holder, 302 Air pump, 303 Air pump gasket, 304 Pressure relief valve, 305 Air inlet, 306 Cleaning liquid inlet, 307 Waste reservoir air port, 308 Waste liquid inlet, 4 Control module, 5 Lower shell, 501 Battery compartment, 502 Diversion pipe, 503 Anti-clogging piece, 504 First snap joint, 505 Second snap joint, 506 Alignment recess, 6 Liquid reservoir, 601 Elastic rubber strip, 7 Waste reservoir.

DETAILED DESCRIPTION

The technical schemes in the embodiments of the present invention are clearly and completely described in the following with reference to the drawings in the embodiments of the present invention. It is obvious that the described embodiments are only some of the embodiments of the present invention and are not all the embodiments.

Examples of the embodiments are illustrated in the accompanying drawings, where the same or like reference numerals throughout the figures indicates the same or like elements having the same or like functions. The embodiments described below with reference to the accompanying drawings are exemplary and are intended to explain the present invention instead of being construed as limiting the present invention.

Figure 2:
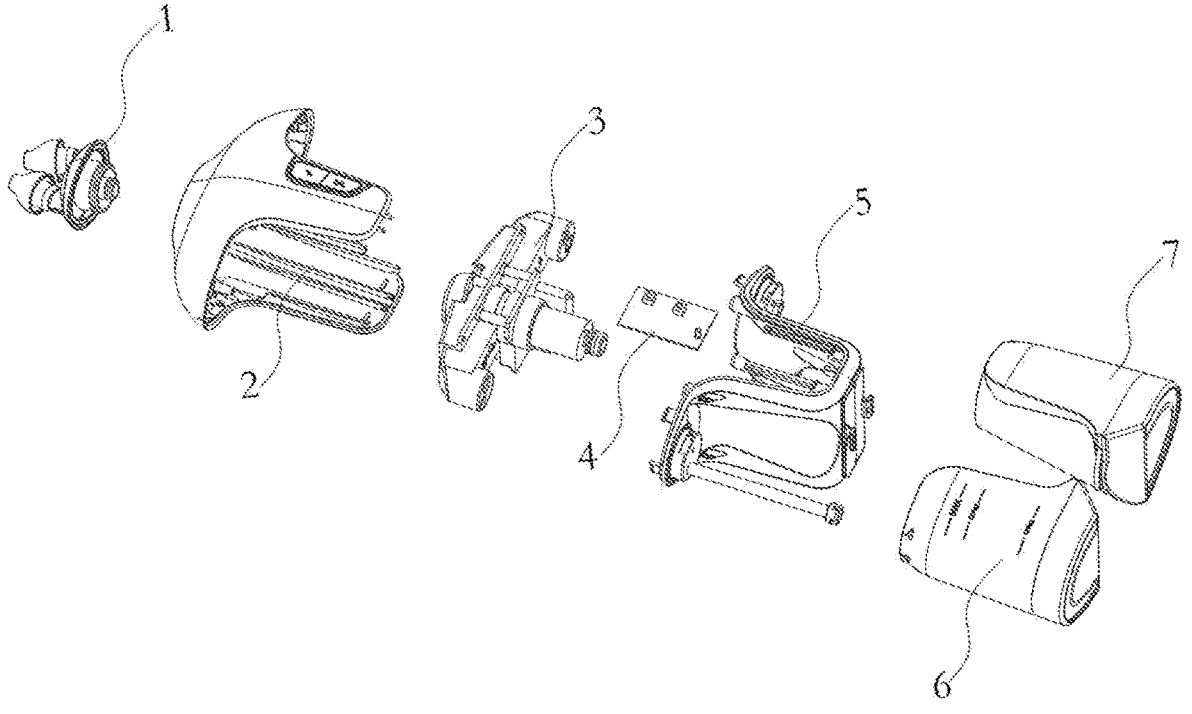
FIG. 2 is an exploded view of a nasal cavity cleaner of the present invention.

Referring to FIGS. 1 and 2, the present invention provides a technical scheme of a positive-pressure double-nozzle nasal cavity cleaner featuring double pressure protection including, among other things, a nose washing end 1, an upper shell 2, a core module 3, a control module 4, a lower shell 5, a liquid reservoir 6 and a waste reservoir 7. The nose washing end 1 is fixed to the upper shell 2 in a pluggable manner, which means that the nose washing end can be mounted and dismounted by directly plugged in and pulling out. After use, the nose washing end can be directly removed and washed under a faucet. The lower shell 5 and the upper shell 2 are connected via snap fit, the liquid reservoir 6 and the waste reservoir 7 are installed on the lower shell 5, and the core module 3, the control module 4 and a power module 6 are fixed inside the upper shell 2.

Figure 3:
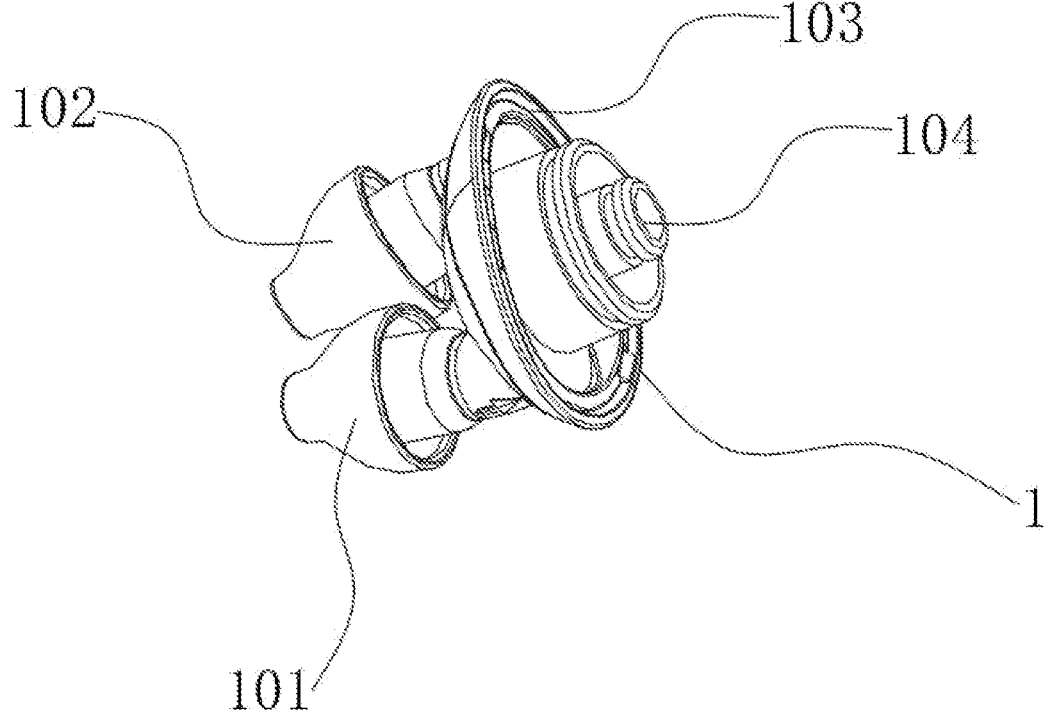
FIG. 3 is a schematic diagram of a nose washing end of a nasal cavity cleaner of the present invention.
Figure 4:
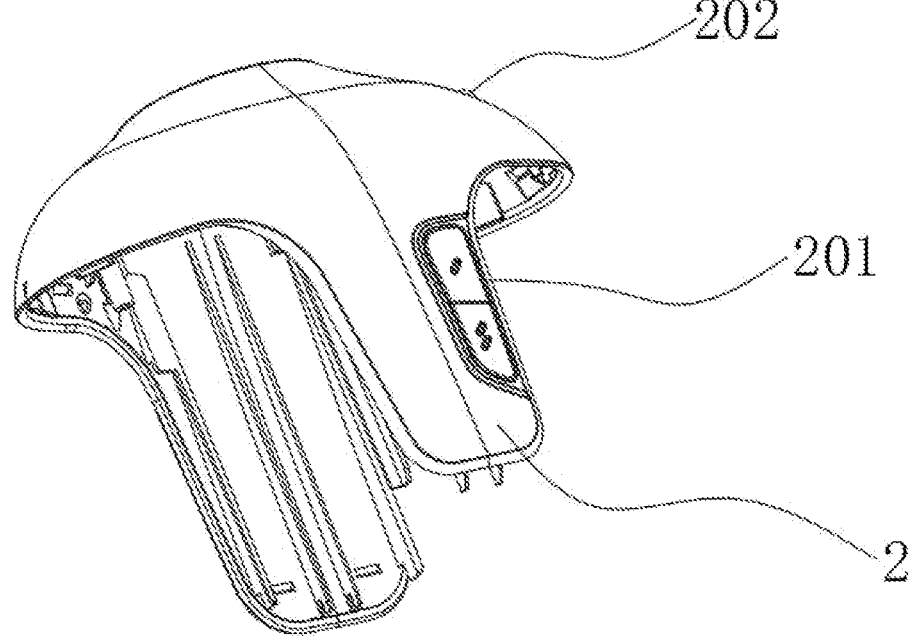
FIG. 4 is a schematic diagram of an upper shell of a nasal cavity cleaner of the present invention.

Please refer to FIG. 3. The nose washing end 1 is rotatably connected to a top portion of the upper shell 2. The nose washing end 1 is composed of a silicone washing nozzle 101, a silicone backflow nozzle 102 and a rotary connecting base 103. The silicone washing nozzle 101 and the silicone backflow nozzle 102 are respectively fixed to two sides of a top portion of the rotary connecting base 103, and a bottom of the rotary connecting base 103 is provided with a water pipe connector 104. The nose washing end 1 is used to connect left and right nostrils, and the nose washing end can be rotated. If a cleaning liquid enters from the left nostril and exits from the right nostril during cleaning, by rotating the nose washing end by 180 degrees, the inflow and outflow directions of the cleaning liquid inside the nostrils can be changed, that is, the cleaning liquid now enters from the right nostril and exits from the left nostril.

Figure 5:
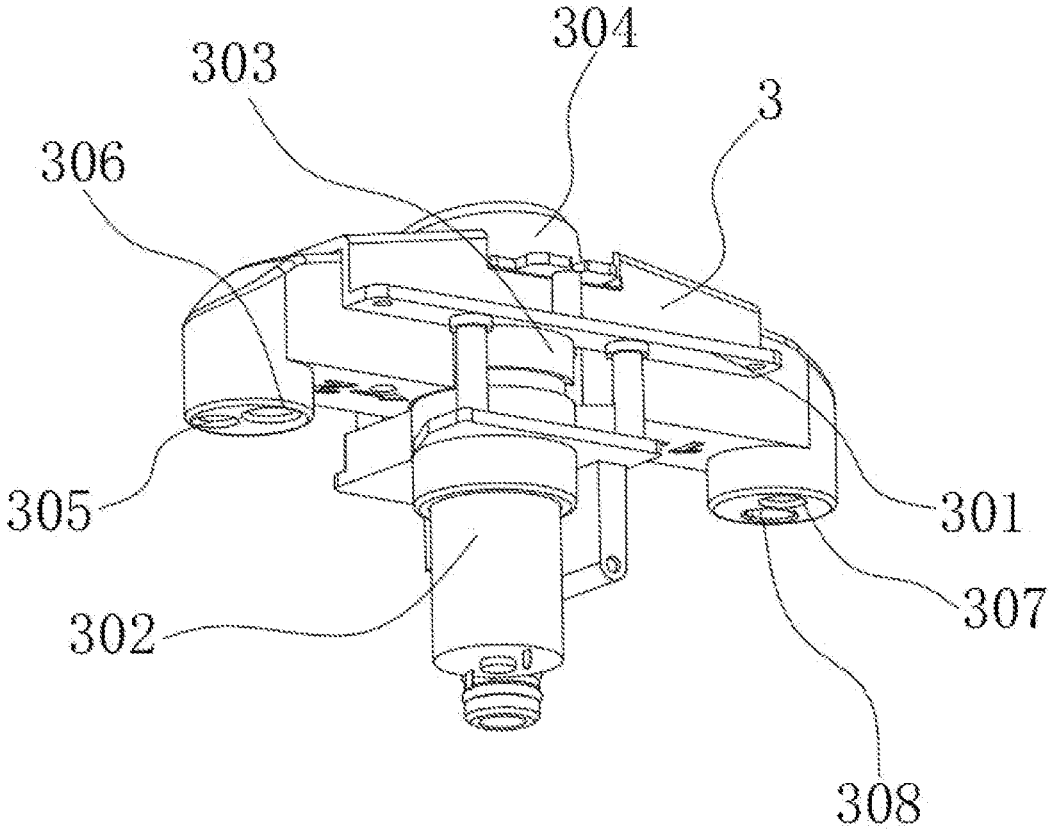
FIG. 5 is a schematic diagram of a core module of a nasal cavity cleaner of the present invention.
Figure 6:
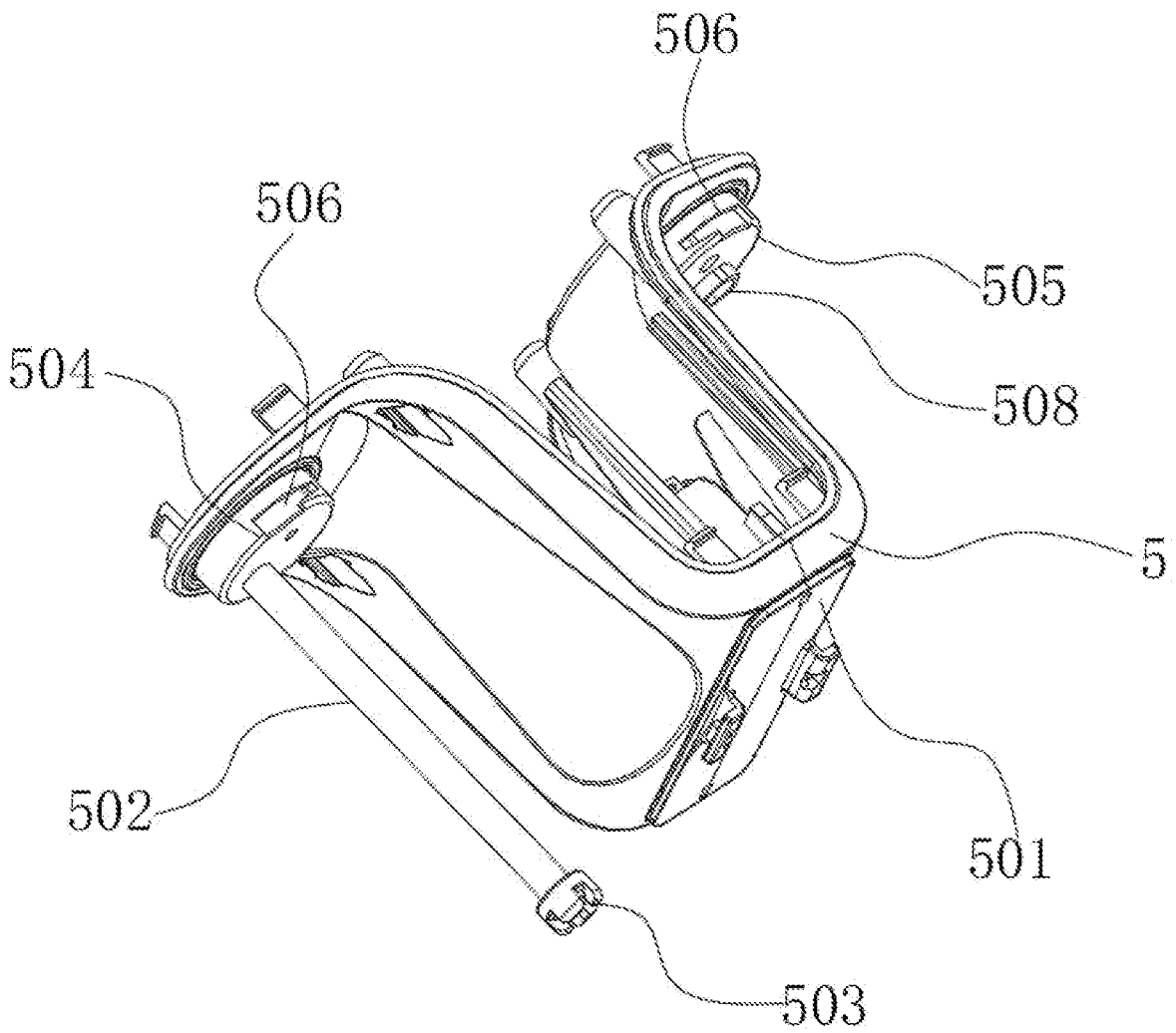
FIG. 6 is a schematic diagram of a lower shell of a nasal cavity cleaner of the present invention.
Figure 7:
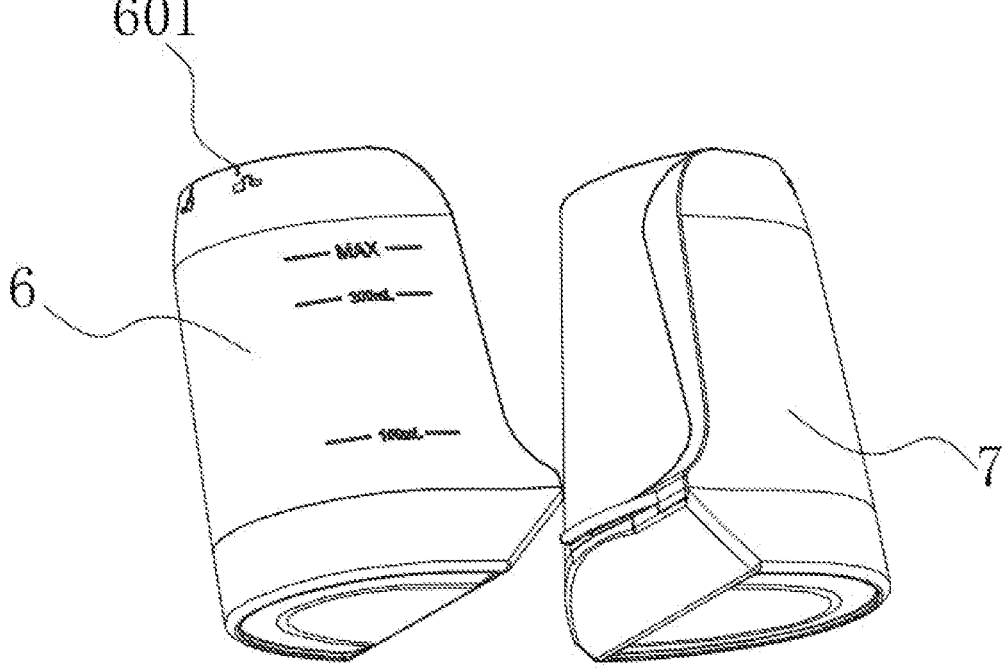
FIG. 7 is a schematic diagram of a liquid reservoir and a waste reservoir of a nasal cavity cleaner of the present invention.
Figure 8:
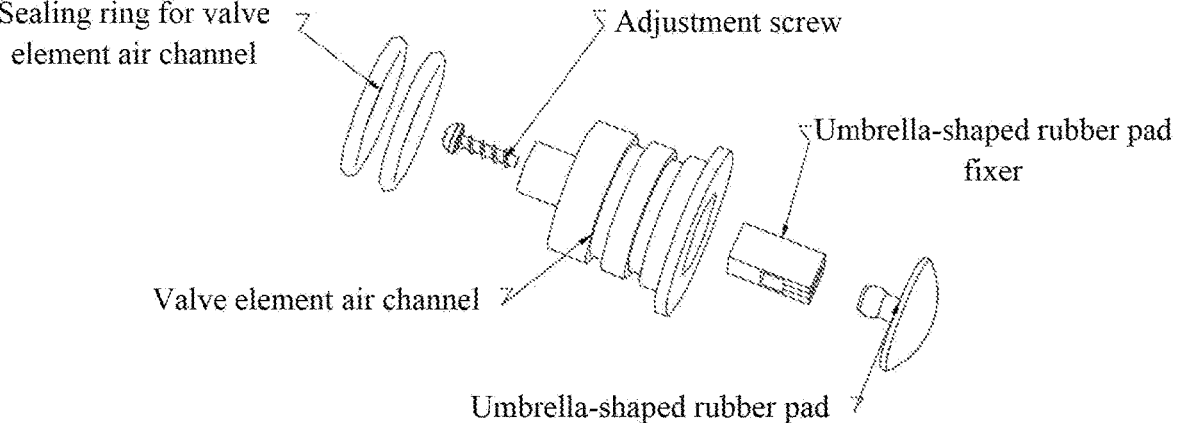
FIG. 8 is a schematic diagram of a pressure relief valve of a nasal cavity cleaner of the present invention.

Please refer to FIGS. 2, 5 and 6. Both the core module 3 and the control module 4 are installed in the upper shell 2. The upper shell 2 is provided with an integrated soft rubber key 201 and a waste reservoir vent hole 202. The integrated soft rubber key 201 is provided with a soft rubber key and an indicator light. An air pump holder 301 is fixed in a middle of the core module 3, and an air pump 302 is fixed on the air pump holder 301. A joint between the air pump 302 and the core module 3 is provided with an air pump gasket 303. One side of the core module 3 is provided with an air inlet 305 and a cleaning liquid inlet 306, the other side of the core module 3 is provided with a waste reservoir air port 307 and a waste liquid inlet 308, and a pressure relief valve 304 is arranged inside the core module 3. One end of the pressure relief valve 304 is provided with an air inlet pipeline, an air outlet pipeline and a cleaning liquid channel, and the other end is provided with a waste liquid channel and a waste reservoir air inlet line. One end of the air inlet pipeline communicates with the air inlet 305, and the other end communicates with the air inlet line of the air pump 302. The air outlet pipeline communicates with an air outlet line of the air pump 302, and the air outlet line communicates with the outside. One end of the cleaning liquid channel communicates with the cleaning liquid inlet 306, and the other end communicates with the silicone washing nozzle 101 through the water pipe connector 104. One end of the waste liquid channel communicates with the waste liquid inlet 308, and the other end communicates with the silicone backflow nozzle 102 through the water pipe connector 104. One end of the waste reservoir air inlet line communicates with the waste reservoir air port 307, and the other end communicates with the waste reservoir vent hole 202.

The core module 3 is mainly used to provide a safe and stable positive pressure air source, and is connected to the nose washing end, the liquid reservoir 6 and the waste reservoir 7.

The control module 4 is mainly used to control the start and stop of the cleaner, and has two operation modes: high-voltage operation and low-voltage operation.

The pressure relief valve 304 includes a valve element air channel, an umbrella-shaped rubber pad, an adjustment screw, and an umbrella-shaped rubber pad fixer. The valve element air channel communicates with both the air inlet channel and the air outlet channel of the air pump 302, and the umbrella-shaped rubber pad is nested on the umbrella-shaped rubber pad fixer which is positioned and fixed by the adjustment screw.

The control module 4 consists of a control key and a control circuit. The control key is welded to a control terminal pin of the control circuit, and the control key corresponds to the integrated soft rubber key 201 in position. The control module 4 is provided with a high-voltage control module and a low-voltage control module. A power supply port of the control module 4 is connected to a power connector of a battery compartment 501 through a power line, and a control port of the control module 4 is connected to an on-off control unit of the air pump 302 and the pressure relief valve 304 through a control line.

Based on the above description, the working principle of the pressure relief valve is as follows. Air pressure output by the air pump 302 enters the valve element air channel, and part of the air pressure will be released through the elastic deformation of the umbrella-shaped rubber pad. By locking or loosening the adjustment screw, that is, locking or loosening the umbrella-shaped rubber pad fixer, the umbrella-shaped rubber pad will be driven to be locked or loosened, and air pressure released by the air through the umbrella-shaped rubber pad will also change accordingly. When the tightness of the umbrella-shaped rubber pad is well adjusted through the adjustment screw, the air pressure of the air pump system can be stabilized at a set pressure value. Such automatic mechanical pressure relief and pressure stabilization means has the advantages of quick response, low cost, simple structure and high reliability.

Referring to FIGS. 1, 2, 4 and 5, the lower shell 5 and the upper shell 2 are connected via snap fit, a connecting portion of the lower shell 5 is wrapped with an integrated waterproof sealing ring, a bottom of the lower shell 5 is provided with the battery compartment 501, one end of the lower shell 5 is provided with a first snap joint 504, and the other end is provided with a second snap joint 505. The first snap joint 504 is connected to a cleaning liquid diversion pipe 502 and a first air hole, which respectively communicate with the cleaning liquid inlet 306 and the air inlet 305. The second snap joint 505 is provided with a waste liquid recovery pipe 508 and a second air hole, which respectively communicate with the waste liquid inlet 308 and the waste reservoir air port 307.

An anti-clogging piece 503 is connected to the diversion pipe 502, and the inside of the diversion pipe 502 is provided with a filter screen which is of a split structure. The split design of the filter screen in the diversion pipe of the reservoir can prevent foreign matter from entering the diversion pipe and affecting the washing effect of the cleaner.

The liquid reservoir 6 and the waste reservoir 7 are connected to the first snap joint 504 and the second snap joint 505 respectively through elastic rubber strips 601.

Outer walls of two ends of a joint between the upper shell 2 and the lower shell 5 are provided with reference lines respectively, outer walls of the liquid reservoir 6 and the waste reservoir 7 are provided with unlocking symbols, the elastic rubber strips 601 are fixed to inner walls of the liquid reservoir 6 and the waste reservoir 7 respectively, outer walls of the first snap joint 504 and the second snap joint 505 are provided with alignment recesses 506 respectively, and the elastic rubber strips 601 on the inner walls of the liquid reservoir 6 and the waste reservoir 7 are respectively in snap-fit with the alignment recesses 506 on the outer walls of the first snap joint 504 and the second snap joint 505.

Figure 9:
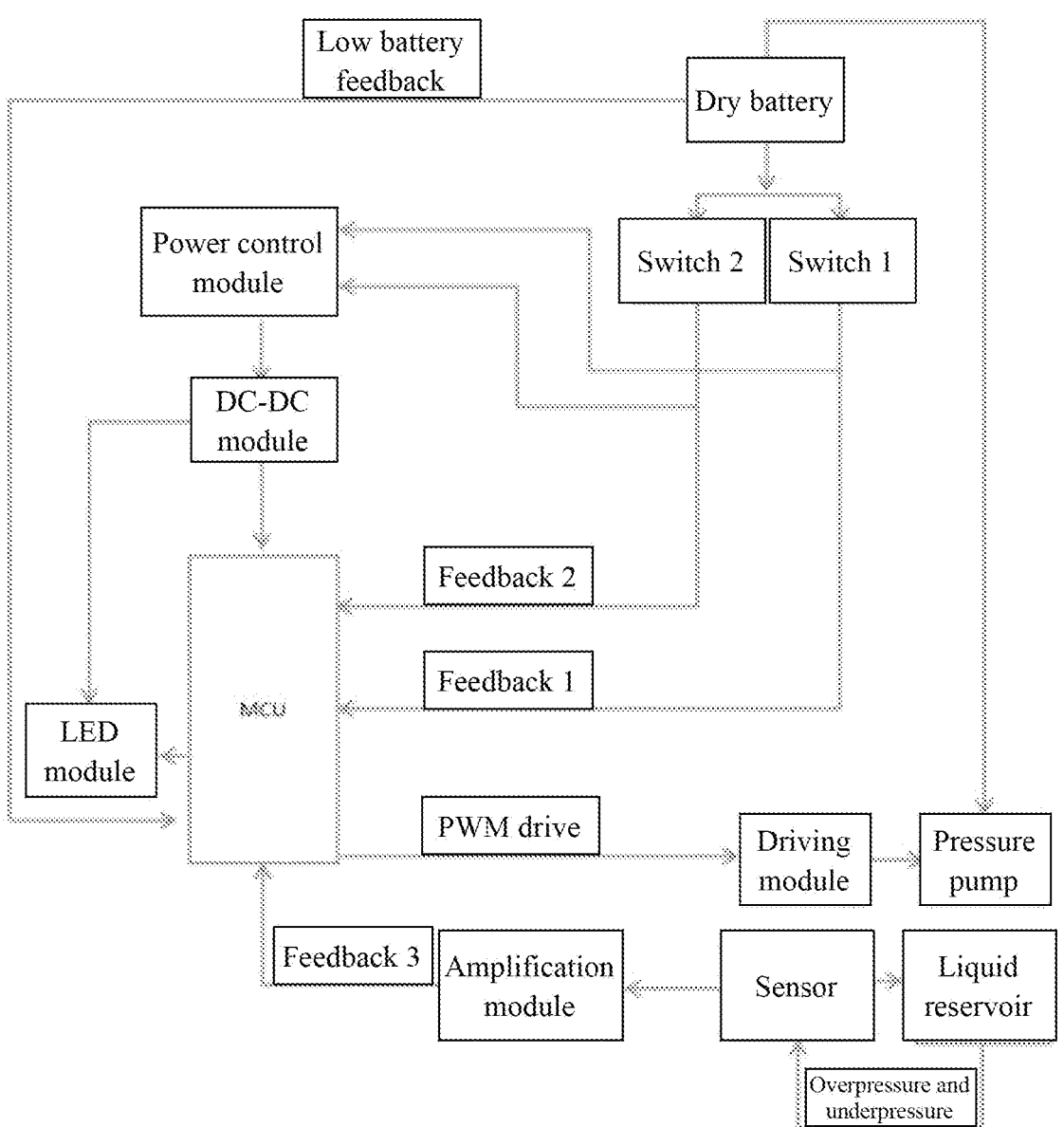
FIG. 9 is a system block diagram of the present invention.

Please refer to FIG. 9, which is a schematic diagram of the working principle of an electronic pressure relief part of the device. Pressure inside the whole cleaner system and nasal cavity is monitored in real time through a built-in air pressure sensor, and system software in the control circuit automatically adjusts a PWM driving duty ratio according to monitored information. In this case, driving power of the driving air pump will change accordingly. After the device is started, the nasal cavity of a user will be slowly filled with the cleaning liquid in the liquid reservoir, and the air pressure sensor will then monitor whether a current air pressure value is reasonable, safe and comfortable for the user in real time according to the physiological structure of the nasal cavity and then automatically adjust the pressure for cleaning.

Please refer to FIGS. 10-14 which are circuit diagrams of the present invention.

Figure 10:
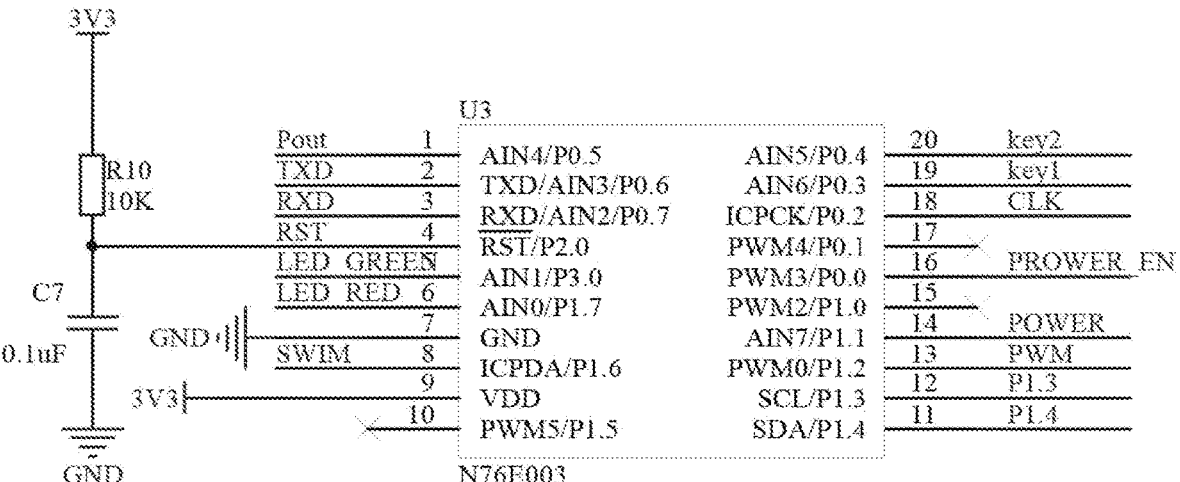
FIG. 10 is an MCU control module circuit.

FIG. 10 shows an MCU module consisting of a power supply 3V3, an N76E003 main control chip and a power-on reset circuit. The main control chip drives an LED and a motor according to feedback signals of other modules. The power supply 3V3 is powered by a DC-DC module, and a reset circuit is formed by the 3V3 power supply, a resistor R10 and a capacitor C7.

In the figures, pin 1 is a sensor signal feedback pin, and pins 2 and 3 are serial ports; pins 5 and 6 are LED drive IO ports; 11 and 12 are reserved IO ports; pin 13 is a motor drive IO port; pin 14 is a low battery charge detection IO port; pin 16 is a control IO port of a power control module; pins 19 and 20 are switch feedback IO ports; and pins 4, 8 and 18, the 3V3 power supply, and GND constitute program burning pins.

Figure 11:
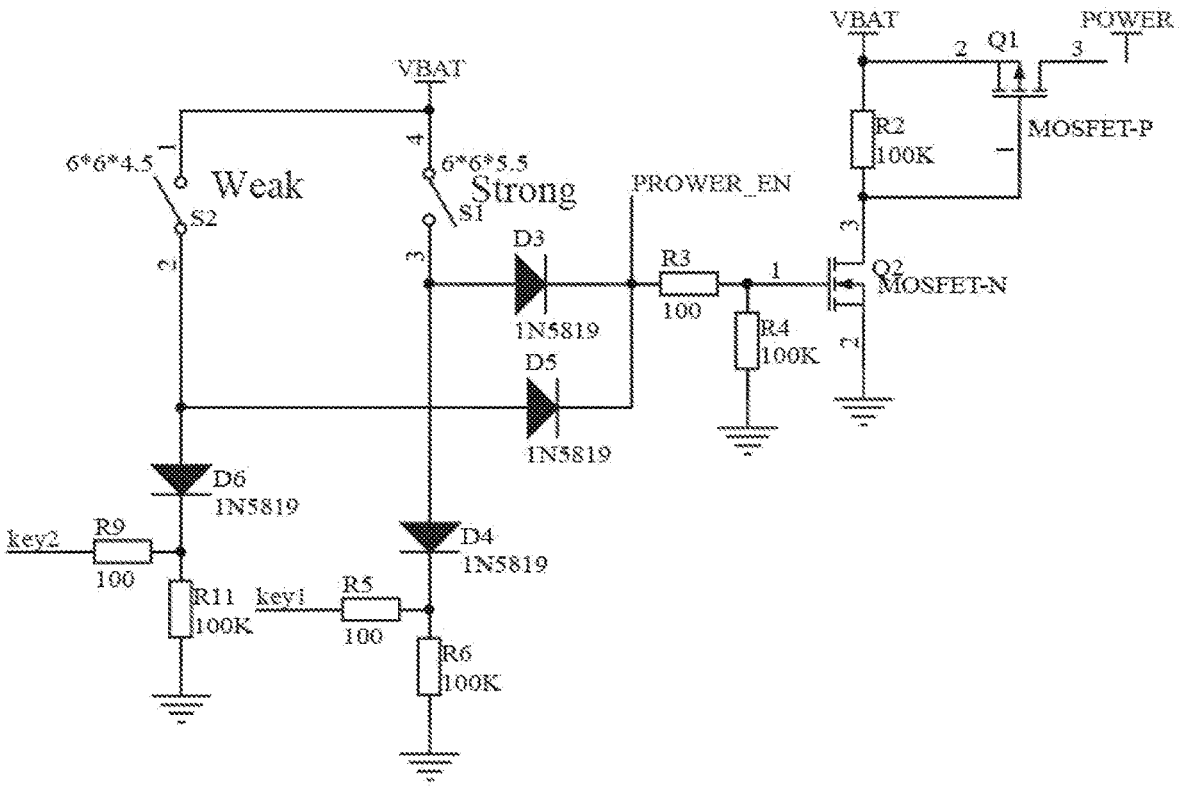
FIG. 11 is a circuit diagram of a power supply part.

FIG. 11 shows a power control and feedback module divided into three parts, that is, a switch part, a feedback part and a control part. Long press of a switch S1 makes the dry battery, namely VBAT provides feedback to an MCU through the switch S1, and diodes D4 and R5, and at the same time, VBAT makes a gate-source voltage difference of a Q2 NMOS transistor larger than a threshold voltage through the switch S1, and D3 and R3. At this point, drain and source electrodes of Q2 are on, so that a gate of Q1 is grounded. Then a source-gate voltage difference of a Q1 PMOS transistor is greater than the threshold voltage, drain and source electrodes of Q1 are on, and VBAT flows to a back-end circuit POWER. Long press of a switch S2 has the same effects as described above. (PROWER_EN in the figure is a reserved MCU I/O port, with a reserved functional pin).

Figure 12:
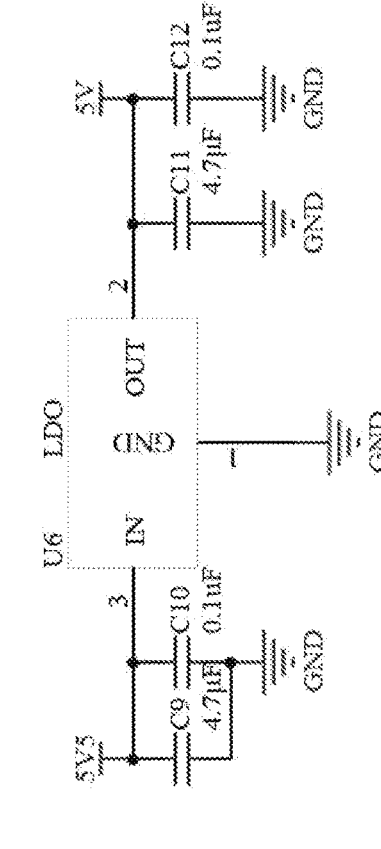
FIG. 12 is a circuit diagram of a DC-DC part.
Figure 12:
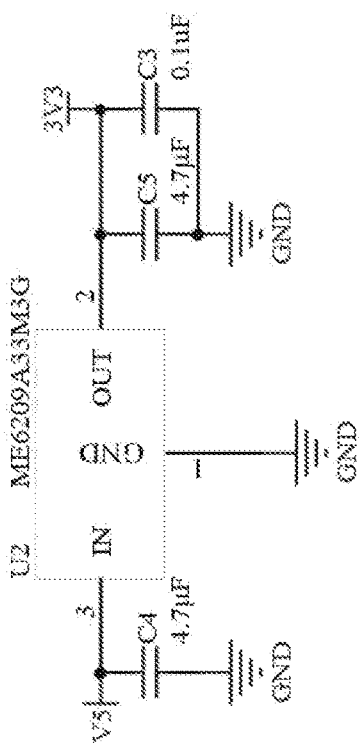
Figure 12:
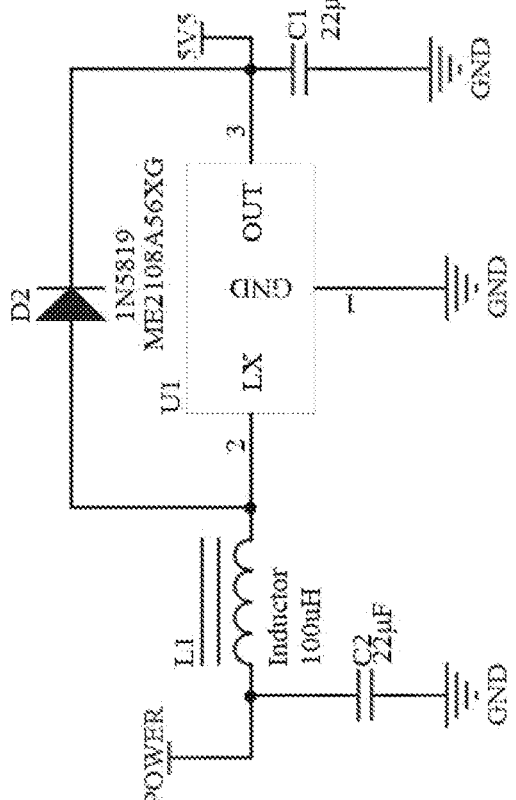
Figure 13:
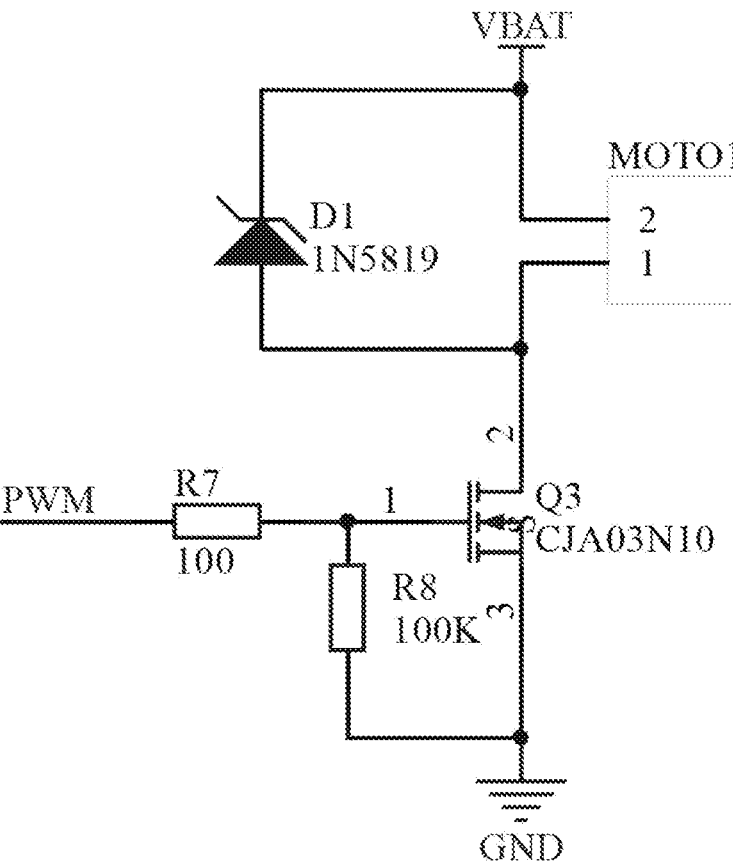
FIG. 13 is a circuit diagram of a PWM module.
Figure 14:
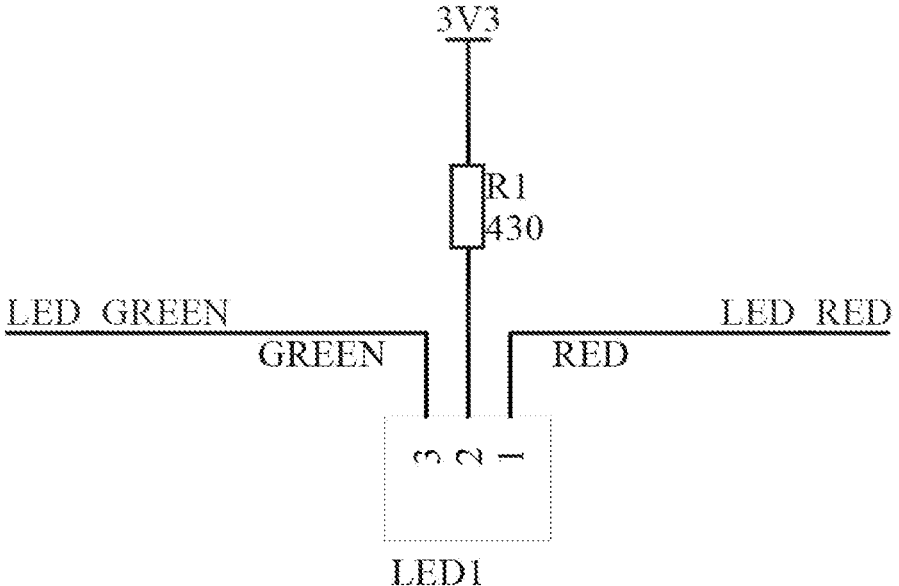
FIG. 14 is a circuit diagram of an LED module.
Figure 15:
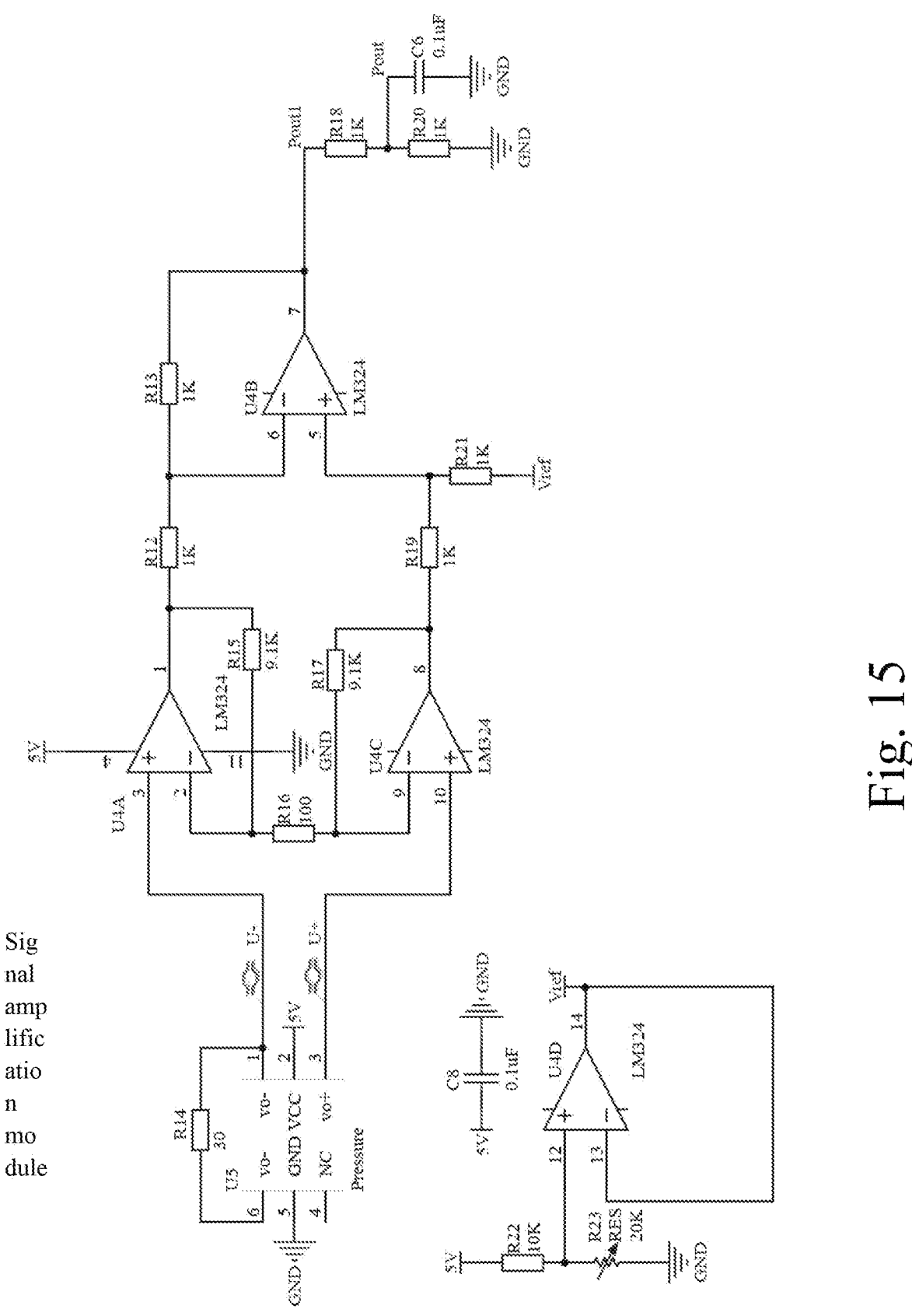
FIG. 15 is a sensor signal amplification module.

FIG. 12 is a DC-DC module which is composed of a boost circuit and two voltage stabilizing circuits. A power supply POWER raises a POWER voltage to 5V5 through a boosting chip U1, a voltage stabilizing chip U2 stabilizes 5V5 to 3V3 to supply power to the MCU and the LED, and U6 stabilizes 5V5 to 5V to supply power to an operational amplifier and the sensor.

When internal pressure of the cleaner exceeds a safe value, the air pressure sensor provides feedback to the MCU through acquisition signals, and the MCU will stop the driving air pump 302. If the air pressure sensor and the MCU fail to accurately monitor and control the pressure of the whole cleaner system, an automatic pressure relief protection device can automatically release pressure to make the pressure inside the cleaner within a safe range, and an electronic and mechanical double pressure protection system ensures the use safety of the product.

This embodiment also provides a use method of the nasal cavity cleaner, which includes the following steps.

At S1, it is checked whether the cleaner is able to work properly. This is realized by installing a battery in a battery compartment, and then pressing Mode 1 and Mode 2 keys of an integrated soft rubber key on an upper shell to check whether they are functioning properly based on indicator lights.

At S2, a nose wash is prepared and loaded. This is realized by holding a shell with the right hand and a liquid reservoir with the left hand, rotating the liquid reservoir counterclockwise, removing the liquid reservoir when an unlocking symbol on the liquid reservoir is aligned with a reference line on a cleaner body, and then introducing warm normal saline into the liquid reservoir as needed.

Further, the normal saline may be any one of a finished pharmaceutical product of normal saline or self-made normal saline with a concentration of 0.9%.

If self-made saline is used, the following points need to be noted.

A. Nose washing salt: Saline or normal saline made from special nose washing salt, instead of ordinary edible salt, must be used for nose washing. Common salt used now is mostly iodized salt, which is inappropriate for nose washing. Because of the abundant capillaries in the nasal cavity, any misuse may cause damage to the human body.

B. Water: Water for preparing nose washing saline must be pure water or cold boiled tap water. Tap water cannot be used directly. First, bacteria in tap water may infect the nasal cavity; and second, tap water often contains added ingredients, which may cause irritation to the nasal cavity. In general, using tap water will aggravate the symptoms of rhinitis.

C. Water temperature: Water temperature should not be too high or too low, preferably around 37° C., which is the normal body temperature.

D. Concentration: The concentration of normal saline is 0.9%, and preparation should be done on this basis. Generally, 2.75 g of nose washing salt is mixed with 250 ml of water. The concentration should not be too high or too low. 0.9% normal saline is the most suitable for nasal cilia swinging, and a concentration too low or too high cannot realize the ideal effect.

If a finished pharmaceutical product of normal saline is used, the following should be noted.

If a finished product of normal saline from a pharmacy is used, the only factor to be considered is water temperature. For rhinitis, normal saline (isotonic) or 1%-2% hypertonic saline is recommended to wash the nasal cavity, which can remove nasal irritants, allergens and inflammatory secretions, reduce nasal mucosa edema and improve mucociliary clearance.

To sum up, isotonic saline (0.9%) is recommended for daily care. Isotonic saline is close to the osmotic pressure of nasal mucosa, and has little irritation, especially suitable for children.

At S3, the liquid reservoir is installed. This is realized by holding the shell with the right hand and the liquid reservoir with the left hand, and inserting the liquid reservoir into the cleaner body and rotating the liquid reservoir clockwise when the unlocking symbol on the liquid reservoir is aligned with the reference line on the cleaner body, till a locking symbol on the liquid reservoir is aligned with a reference line on the cleaner body, at which point an elastic positioning bead just slides into a positioning recess of the liquid reservoir, marking the completion of liquid reservoir installation.

At S4, the cleaner is held with a key facing a human body, and a nose washing end is caused to slowly approach nostrils so as to be inserted into the nostrils, and it should be ensured that the nose washing end completely blocks the nostrils.

At S5, the key is pressed to start nasal cavity cleaning.

At S6, a waste reservoir is removed.

The following points should be noted in use.

I. The mouth should be wide open and breathing is done through the mouth during nose washing.

II. When the Mode 1 or Mode 2 key is pressed, an air pump and a pressure relief valve will start working at the same time, the air pump will output air pressure, the pressure relief valve will adjust the output air pressure, and then constant air pressure will be continuously input into the liquid reservoir; and nose wash in the liquid reservoir will enter an anti-clogging piece under pressure, reach a cleaning liquid channel in the nose washing end through a diversion pipe in the liquid reservoir and a cleaning liquid channel of a machine core, then enter one nostril, next bypass the nasopharynx or flow out from the other nostril to reach a waste liquid channel of the nose washing end after passing through the nasal vestibule, nasal sinuses and nasal passages, then flow to a waste liquid channel of a core module, and finally flow into the waste reservoir.

It should be noted that the nasal cavity cleaner has a high-strength cleaning mode and a low-strength cleaning mode (i.e., Mode 1 and Mode 2), which aim for different symptoms. Those who have never used the cleaner are advised to start from a lower setting and then gradually change to a higher setting. The volume of nose wash can also be increased from 100 ML to 200 ML.

In the low-strength mode, water spray is gentler and impact force is smaller, while in the high-strength mode, the impact force of the water spray is larger, which is more suitable for patients with many nasal secretions, severe nasal congestion and sinusitis. The cleaner has a pressure relief protection function, and both modes will not irritate or hurt the nasal mucosa, and will also avoid otitis media.

III. Rotating the nose washing end can change the inflow and outflow directions of the cleaning liquid inside the two nostrils, and alternate washing should last about 1-2 minutes in total. Both nostrils need to be cleaned. Swallowing a small amount of saline is harmless.

IV. When the nose wash in the liquid reservoir is used up, the nose washing end can stay in the nostrils for 2-3 seconds to remove the remaining saline from the nasal cavity, or a user can gently swing his/her head from side to side after washing, and then exhale through the nose to remove the remaining saline from the nasal cavity.

V. Nose washing is usually conducted once in the morning and once in the evening, and at least 200 ml is recommended per side of the nasal cavity each time.

VI. No talking and no swallowing during washing. Nose washing is not suitable for those with nasal bleeding and acute middle ear infection.

The cleaning principle of a double-nozzle positive-pressure electric nose cleaner is as follows.

①Nasal cavity cleaning mainly relies on the sterilization effect of normal saline and the impact of water flow, which help eliminating pathogenic bacteria or dirt accumulated in the nasal cavity, even allergens, bacteria, viruses and purulent nasal discharge accumulated in paranasal sinuses. Through the washing of saline water, the nasal cavity can have a normal physiological environment again, and the root cause of inflammation can disappear, thus eliminating the symptoms of inflammation, restoring the function of nasal cilia, restoring the self-detoxification function of the nasal cavity, and achieving the purposes of protecting the nasal cavity and speeding up the recovery of nasal cavity health.

②The pressure of the positive-pressure double-nozzle nose cleaner is proper to solve the problem that if the pressure of saline water entering the nasal cavity is too high, nasal tissue may be damaged and other complications may be caused. Nasal cavity structures are not exactly the same for everyone. Adults and children have different nasal cavity structures, which can bear different pressures. This nose cleaner has a pressure relief protection function, which fundamentally guarantees the safety of users.

The above embodiments are only preferred ones of the present invention, and the scope of protection of the present invention is not limited thereto. Any equivalent substitution or change made by any person skilled in the art within the technical scope disclosed by the present invention according to the technical scheme and inventive concept of the present invention shall be included within the scope of protection of the present invention.

What is claimed is:

1. A positive-pressure double-nozzle nasal cavity cleaner featuring double pressure protection, comprising:
a shell having a lower shell,
a cleaning liquid container,
a nose washing end, and
a waste liquid recovery container,
wherein the positive-pressure double-nozzle nasal cavity cleaner further comprises a core module, a middle of the core module is provided with an air pump, a cleaning liquid inlet is provided at a first side of the air pump, a waste liquid inlet is provided at a reverse side, relative to the first side, of the air pump,
the lower shell has a U-shaped structure; a cleaning liquid diversion pipe is provided at one side of the U-shaped structure, and a waste liquid recovery pipe is provided at an other side of the U-shaped structure; the cleaning liquid diversion pipe communicates with the cleaning liquid inlet and the cleaning liquid container, and the waste liquid recovery pipe communicates with the waste liquid inlet and the waste liquid recovery container;
the air pump extends beneath the cleaning liquid diversion pipe into an interior of the U-shaped structure;
the air pump provides a positive pressure source, the positive pressure source drives a cleaning liquid to flow by increasing air pressure in the cleaning liquid container, an automatic pressure relief mechanism is arranged in an internal passage to maintain the air pressure, the automatic pressure relief mechanism comprises a mechanical pressure relief part and an electronic feedback part, the electronic feedback part and a driving part in the positive pressure source are controlled by a control module, and the control module stabilizes hydraulic pressure in a liquid passage at a preset value,
the nose washing end is rotatable, such that inflow and outflow directions of the cleaning liquid inside nostrils are capable of being changed.

2. The positive-pressure double-nozzle nasal cavity cleaner featuring double pressure protection of claim 1, wherein the nose washing end, the cleaning liquid container and the waste liquid recovery container are all detachably connected to the shell of the cleaner.

3. The positive-pressure double-nozzle nasal cavity cleaner featuring double pressure protection of claim 2, wherein the nose washing end comprises two silicone nozzles, and when the two silicone nozzles are inserted into the nasal cavity, a flow passage of liquid flowing out of the cleaning liquid container, passing through the nasal cavity and then flowing into the waste liquid recovery container is formed.

4. The positive-pressure double-nozzle nasal cavity cleaner featuring double pressure protection of claim 2, wherein the mechanical pressure relief part is a pressure relief valve, and a preset pressure value of the pressure relief valve is adjustable.

5. The positive-pressure double-nozzle nasal cavity cleaner featuring double pressure protection of claim 1, wherein the electronic feedback part comprises an air pressure sensor arranged in a passage of the positive pressure source, the air pressure sensor sends air pressure data to a feedback module, and the control module adjusts an output of the positive pressure source according to the air pressure data received by the feedback module to stabilize water pressure in the water passage.

6. The positive-pressure double-nozzle nasal cavity cleaner featuring double pressure protection of claim 5, wherein the feedback module is provided with at least two settings, which are controlled by switches, and each setting corresponds to a preset water pressure value.

7. A use method of the positive-pressure double-nozzle nasal cavity cleaner featuring double pressure protection of claim 1, comprising the following steps:
S1. checking whether the cleaner is able to work properly;
S2. after confirming that the cleaner is able to work properly, preparing a nasal wash and loading the nasal wash into the cleaner, wherein an appropriate amount of warm normal saline is loaded into the cleaning liquid container as needed;
S3. installing the cleaning liquid container onto a cleaner body;
S4. holding the cleaner with a key facing a human body, and moving the nose washing end toward the nostrils so as to be inserted into the nostrils, and ensuring that the nose washing end completely blocks the nostrils;
S5. pressing the key to start nasal cavity cleaning; and
S6. removing the waste liquid recovery container.

8. The use method of the positive-pressure double-nozzle nasal cavity cleaner featuring double pressure protection of claim 7, wherein a temperature of the cleaning liquid in S2 is 37° C.

9. The use method of the positive-pressure double-nozzle nasal cavity cleaner featuring double pressure protection of claim 7, wherein in S1, it is checked whether there is a battery in a battery compartment, and it is checked whether mode one and mode two keys of an integrated soft rubber key on an upper shell function properly based on indicator lights activated by pressing the key.

10. The positive-pressure double-nozzle nasal cavity cleaner featuring double pressure protection of claim 1, wherein the nose washing end comprises a washing nozzle, a backflow nozzle and a rotary connecting base, the washing nozzle and the backflow nozzle are fixed to a top portion of the rotary connecting base, and a bottom of the rotary connecting base is provided with a water pipe connector; the rotary connecting base is configured to rotate to change relative positions of the washing nozzle and the backflow nozzle on the cleaner, thereby changing inflow and outflow directions of the cleaning liquid inside the nostrils.

11. The positive-pressure double-nozzle nasal cavity cleaner featuring double pressure protection of claim 4, wherein the pressure relief valve comprises a valve element air channel, an umbrella-shaped rubber pad, an adjustment screw, and an umbrella-shaped rubber pad fixer;
wherein the valve element air channel communicates with both an air inlet channel and an air outlet channel of the positive pressure source; the umbrella-shaped rubber pad is connected on the umbrella-shaped rubber pad fixer, and the umbrella-shaped rubber pad fixer is positioned and fixed by the adjustment screw; a tightness of the umbrella-shaped rubber pad is adjusted through the adjustment screw, such that the air pressure in the cleaning liquid container is capable of being stabilized at a set pressure value.

12. The positive-pressure double-nozzle nasal cavity cleaner featuring double pressure protection of claim 2, wherein the shell comprises an upper shell and the lower shell, the lower shell and the upper shell are connected via snap fit, the cleaning liquid container and the waste liquid recovery container are installed on the lower shell, and the positive pressure source, the automatic pressure relief mechanism and the control module are fixed between the upper shell and the lower shell.

13. The positive-pressure double-nozzle nasal cavity cleaner featuring double pressure protection of claim 1, wherein an air pump holder is fixed in the middle of the core module, and the air pump is fixed on the air pump holder; a joint between the air pump and the core module is provided with an air pump gasket.

14. The positive-pressure double-nozzle nasal cavity cleaner featuring double pressure protection of claim 1, wherein one end of the lower shell is provided with a first snap joint, and an other end of the lower shell is provided with a second snap joint; elastic rubber strips are fixed to inner walls of the cleaning liquid container and the waste liquid recovery container respectively; the cleaning liquid container and the waste liquid recovery container are connected to the first snap joint and the second snap joint respectively through the elastic rubber strips.

15. The positive-pressure double-nozzle nasal cavity cleaner featuring double pressure protection of claim 14, wherein outer walls of the first snap joint and the second snap joint are provided with alignment recesses respectively, and the elastic rubber strips on the cleaning liquid container and the waste liquid recovery container are respectively in snap-fit with the alignment recesses on the outer walls of the first snap joint and the second snap joint.

16. The positive-pressure double-nozzle nasal cavity cleaner featuring double pressure protection of claim 1, wherein a bottom of the U-shaped structure is provided with a battery compartment.

17. The positive-pressure double-nozzle nasal cavity cleaner featuring double pressure protection of claim 1, wherein the cleaning liquid container and the waste liquid recovery container are symmetrically provided at the one side and the other side sides of the U-shaped structure.

* * * * *